United States Defensive Publication [19] (H) [11] T100,505

Morrow et al. [43] Apr. 7, 1981

[54] TRIAZOLO[4,3-a]PYRIDIN-3(2H)-ONES

[76] Inventors: Duane F. Morrow, 8200 Berry Dr., Evansville, Ind. 47710; Yao H. Wu, 9200 Farmington Dr., Evansville, Ind. 47712

[21] Appl. No.: 130,900

[22] Filed: Mar. 17, 1980

[51] Int. Cl.[3] ..... C07D 00/00

[52] U.S. Cl. ..... 542/444; 544/366; 424/250

[57] ABSTRACT

Triazolo[4,3-a]pyridin-3-(2H)-one derivatives containing a 4-(optionally substituted phenyl)piperazinyl component attached to the two position of the triazolo-[4,3-a]pyridine component via a divalent radical such as $-(CH_2)_5-$, $-(CH_2)_6-$, $-CH_3CH(CH_3)CH_2-$, $-CH_2C(CH_3)_2CH_2-$, $-CH_2CH{=}CHCH_2-$, $-CH_2C{\equiv}CCH_2-$, $-CH_2CH_2OCH_2CH_2-$ or a divalent cycloalkylene radical of 3 to 6 carbon atoms are disclosed. The compounds are useful in that they exhibit central nervous system pharmacological properties in standard laboratory tests considered predictive of analgetics, anti-psychotic (neuroleptics), antidepressant and antianxiety utility. Examples of specific embodiments of the invention are compounds having the formula

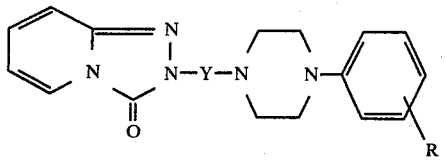

| Y | R |
|---|---|
| 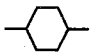 | 3-Cl |
| 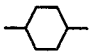 | H |
| 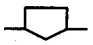 | 3-Cl |
| 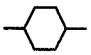 | 3-$CF_3$ |
| 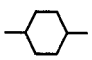 | 4-F |
| $CH_2CH{=}CHCH_2$ | 3-Cl |
| $CH_2C{\equiv}CCH_2$ | 3-Cl |
| $(CH_2)_5$ | 3-Cl |
| $(CH_2)_5$ | 4-$CH_3O$ |
| $(CH_2)_5$ | 2-$CH_3$ |
| $(CH_2)_6$ | 3-Cl |
| $CH_2C(CH_3)_2CH_2$ | 3-Cl |
| $CH_2CH(CH_3)CH_2$ | 3-$CF_3$ |
| $CH_2CH_2OCH_2CH_2$ | 3-Cl |

1 Claim, No Sheets Drawing,

12 Pages Specification

The file of this unexamined application may be inspected and copies thereof may be purchased (849 O.G. 1221, Apr. 9, 1968).